United States Patent [19]

Sauber

[11] Patent Number: 5,599,702
[45] Date of Patent: Feb. 4, 1997

[54] **D-AMINO ACID OXIDASE FROM *TRIGONOPSIS VARIABILIS* IMMOBILIZED ON POROUS COPOLYMER BEADS**

[75] Inventor: Klaus Sauber, Bad Soden am Taunus, Germany

[73] Assignee: Hoechst Aktiengesellschaft, Frankfurt am Main, Germany

[21] Appl. No.: 443,017

[22] Filed: May 17, 1995

Related U.S. Application Data

[63] Continuation of Ser. No. 805,514, Dec. 12, 1991, abandoned.

[30] Foreign Application Priority Data

Dec. 24, 1990 [DE] Germany .......................... 40 41 755.7

[51] Int. Cl.⁶ .......................... C12N 11/06; C12N 11/18; C12N 11/08; C12P 35/00
[52] U.S. Cl. .............................. 435/181; 435/47; 435/49; 435/175; 435/180; 435/191; 435/255.1; 435/911
[58] Field of Search .................... 435/47, 48, 49, 435/175, 180, 181, 191, 255.1, 911

[56] References Cited

U.S. PATENT DOCUMENTS

| | | | |
|---|---|---|---|
| 3,801,458 | 4/1974 | Fildes et al. | 195/29 |
| 4,460,686 | 7/1984 | Hartmeier | 435/175 X |
| 4,568,706 | 2/1986 | Noetzel et al. | 521/56 |
| 4,906,715 | 3/1990 | Mauz et al. | 526/258 |
| 4,931,476 | 6/1990 | Mauz et al. | 521/34 |
| 5,079,156 | 1/1992 | Mauz et al. | 435/181 |
| 5,130,246 | 7/1992 | Schulz et al. | 435/193 |

FOREIGN PATENT DOCUMENTS

| | | |
|---|---|---|
| 0150350A3 | 8/1985 | European Pat. Off. . |
| WO86/04087 | 7/1986 | WIPO . |

OTHER PUBLICATIONS

Abstract of DE 2421789 "Polyoxymethylene – bonded biologically active compounds useful as selective affinity chromatography absorbent for antibody recovery", Nov. 13, 1975, WPI Acc. No. 75–77263W/47.

Abstract of DE 2552510 "Vinylene-glycol copolymers as biological supports used in affinity chromatography for effecting immunological and enzymatic reactions", Jun. 30, 1977, WPI-ACC No. 77–36264Y/21.

Si-yin Chung et al., "Measurement of Amino Acid Racemization in Alkali–Treated Proteins Using an Immobilized D–Amino Acid Oxidase–Catalase Reactor", Journal of Agricultural and Food Chemistry, 33, 201–204 (1985).

Tetsuya Tosa et al., "Immobilized D–Amino Acid Oxidase Preparation, Some Enzymatic Properties, and Potential Uses", Agricultural and Biological Chemistry 38 (8), 1529–1534 (1974).

*Primary Examiner*—David M. Naff
*Attorney, Agent, or Firm*—Finnegan, Henderson, Farabow, Garrett & Dunner, L.L.P.

[57] ABSTRACT

D-amino acid oxidase (DAO) in purified, partially purified or crude form is immobilized on a porous bead-shaped support that is a copolymer of vinyl acetate and/or vinyl alcohol and a crosslinking agent. A preferred crosslinking agent is N,N'-divinylethyleneurea. The amount of crosslinking agent is 1 to 60% by weight of the copolymer, and acyloxy groups of vinyl acetate may be present on the support as such or may have been hydrolyzed to hydroxyl groups. The support preferably has a mean particle size of 20 to 800 μm and a mean pore diameter of 2 to 10,000 nm. The D-amino acid oxidase is preferably obtained from *Trigonopsis variabilis* and purified by ion exchange chromatography. The D-amino acid oxidase may be covalently bonded to a spacer such as epichlorohydrin or its homolog that is bound to the support. Catalase may also be immobilized.

1 Claim, No Drawings

D-AMINO ACID OXIDASE FROM *TRIGONOPSIS VARIABILIS* IMMOBILIZED ON POROUS COPOLYMER BEADS

This application is a continuation of application Ser. No. 07/805,514, filed Dec. 12, 1991, now abandoned.

DESCRIPTION

D-amino acid oxidase (hereinafter DAO) catalyzes the oxidative deamination of D-amino acids to the corresponding α-keto acids, ammonia and hydrogen peroxide.

In addition to the commercially available DAO from hog kidneys, the enzyme is synthesized by bacteria, yeasts and molds. *Trigonopsis variabilis* stands out among these as the most potent DAO producer. In addition to the use of this enzyme for the separation of racemates of D,L-amino acids and the quantitative determination of D-amino acids in various solutions, its ability to oxidatively deaminate cephalosporin C is particularly noteworthy. This catalytic property is used for the preparation of ζ-ketoadipyl-7-aminocephalosporanic acid and glutaryl-7-aminocephalosporanic acid, which can be subsequently converted to 7-aminocephalosporanic acid by means of an acylase.

German Offenlegungsschrift 22 19 454 (U.S. Pat. No. 3,801,458) describes the conversion of cephalosporin C derivatives by means of activated cells of *Trigonopsis variabilis* CBS 40 95. "Activated" here signifies that the yeast cells have been subjected to a physical and/or chemical process, so that the DAO in the cells is made available for catalyzing the oxidation of cephalosporin C, but is not liberated to a great extent.

The patent application WO 86 04 087 describes the purification and immobilization of DAO from *Trigonopsis variabilis* and the use of DAO for the oxidative deamination of cephalosporin C. However, no details are given about the operational stability, and the immobilization yield is given as 40%.

It was the object of the present invention to improve the stability of D-amino acid oxidase. Surprisingly, it has now been found that coupling D-amino acid oxidase to a support material made of a crosslinked copolymer, substantially comprising vinyl acetate units and/or vinyl alcohol units and units of a crosslinking agent, forms a complex in which the enzyme DAO retains its activity for a long period.

The invention thus relates to an enzyme-coated support material, comprising D-amino acid oxidase and a porous bead-shaped support material, where the support material is a crosslinked copolymer, substantially comprising vinyl acetate units and/or vinyl alcohol units and units of a crosslinking agent, where the units of the crosslinking agent are copolymerized compounds of the formulae

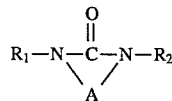

and/or

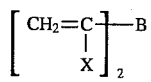

where $R_1$ and $R_2$ in formula (I) can be identical or different and are vinyl, 1-acyloxyvinyl, allyl or 2-acyloxyallyl, A is a divalent hydrocarbon radical having 2 to 8 carbon atoms, B in formula (II) is a divalent hydrocarbon radical having 1 to 8 carbon atoms, and X is acyloxy, where the acyloxy group is a radical having 2 to 18 carbon atoms, the amount of crosslinking agent is 1 to 60% by weight, relative to the polymer, and the acyloxy groups of the vinyl acylate units are present as such, or some or all have been hydrolyzed to hydroxyl groups, and the mean particle size of the beads is 20 to 800 μm and the mean pore diameter is 2 to 10,000 nm. It was surprising that the enzymes in an immobilized form following the coupling to the support mentioned show a storage stability of at least 6 months. In comparison with other known enzyme supports such as, for example, ®Eupergit (Röhm), vinyl-®Sepharose (Kem-en-tec), BrCN-activated-®Sepharose (Pharmacia), the support according to the invention showed a surprisingly high immobilization yield with DAO, and a longer operational stability. Particular preference is given to the use of the vinyl acetate-epoxysupports from Riedel de Haen, for example VA-Epoxy-®Biosynth.

The preparation of the porous, bead-shaped support materials used is disclosed in DE-A 33 44 912, the U.S. equivalents of which are U.S. Pat. Nos. 4,906,715 and 5,079,156, to which reference is made here.

The coupling reaction between the enzymes used according to the invention and the support material is carried out in a known manner, such as is described for example in DE-A 24 07 340 or in the German Patents 22 15 687, 24 21 789 and 25 52 510.

The invention relates to the use of the support material according to the invention for the oxidative deamination of cephalosporin C derivatives.

The term cephalosporin C derivatives means for example compounds such as those of the formula III

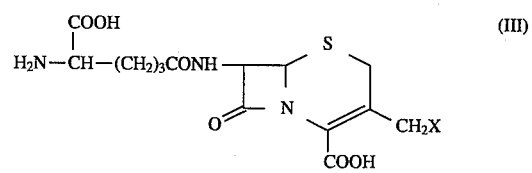

in which
X is an acetate group,
a nucleophile radical,
a heterocycle,
a hydroxyl group or
hydrogen,
and salts thereof.

Cephalosporin C is a compound of the formula IV

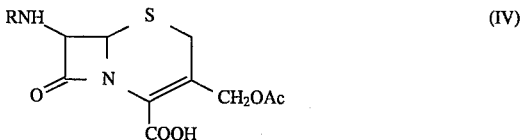

in which R is

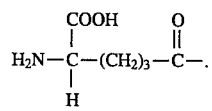

α-Ketoadipyl-7-aminocephalosporanic acid is a compound of the formula IV in which R is

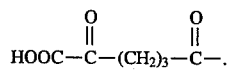

Glutaryl-7-aminocephalosporanic acid is a compound of the formula IV in which R is

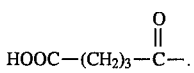

7-Aminocephalosporanic acid is a compound of the formula IV in which R is hydrogen.

Furthermore the invention relates to a process for the preparation of the coated support materials, which comprises incubating a D-amino acid oxidass-containing solution with a porous bead-shaped support material made of a crosslinked copolymer, substantially comprising vinyl acetate units and/or vinyl alcohol units and units of a crosslinking agent, where the units of the crosslinking agent are copolymerized compounds of the formulae

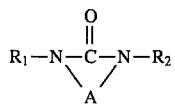

and/or

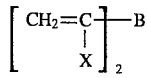

where $R_1$ and $R_2$ in formula (I) can be identical or different and are vinyl, 1-acyloxyvinyl, allyl or 2-acyloxyallyl, A is a divalent hydrocarbon radical having 2 to 8 carbon atoms, B in formula (II) is a divalent hydrocarbon group having 1 to 8 carbon atoms, and X is acyloxy, where the acyloxy group is a radical having 2 to 18 carbon atoms, the amount of crosslinking agent is 1 to 60% by weight, relative to the polymer, and the acyloxy groups of the vinyl acylate units are present as such, or some or all have been hydrolyzed to hydroxyl groups, and the mean particle size of the beads is 20 to 800 μm and the mean pore diameter is 2 to 10,000 nm.

The vinyl acetate units of the support polymer preferably contain 2 to 18 carbon atoms, in particular 2 to 6 carbon atoms, in the acylate radical. Preferably, this is the acetate or propionate radical. Different acylate radicals can also be present in the polymer, i.e. mixtures of the corresponding vinyl acylates can also be used for its preparation.

In the crosslinking agent according to the formula (I), A is preferably a branched or unbranched aliphatic hydrocarbon radical having 2 to 5 carbon atoms, in particular 2 or 3 carbon atoms. Particular preference is given to the ethylene or propylene radical. If $R_1/R_2$ of this formula (I) is 1-acyloxyvinyl or 2-acyloxyallyl, then the acyloxy group therein preferably contains 2 to 18 carbon atoms, in particular 2 to 6 carbon atoms. Preferably acyloxy is the acetate or propionate radical. The $R_1/R_2$ radicals are preferably vinyl. A preferred crosslinker unit in the polymer used according to the invention is correspondingly derived from N,N'-divinylethyleneurea. This crosslinker produces a particularly hydrolysis-resistant coupling. Another preferred representative is N,N'-divinylpropyleneurea.

In the crosslinking agent according to the formula (II), B is preferably a divalent hydrocarbon radical, in particular a branched or unbranched alkylene radical having 2 to 6 carbon atoms, and preferably has the same meaning as described above for the radicals $R_1$ and $R_2$ in the formula (I). A preferred crosslinker of this type is for example 3,3-dimethylpentadiene 2,4-diacetate, which copolymerizes particularly easily with the vinyl acetate.

The amount of units of the crosslinking agent (II) is generally 0 to 100%, in particular 0 to 60%, relative to the total amount of crosslinker units in the polymer.

The total amount of crosslinker units in the support polymer is within the ranges claimed and depends on the degree of crosslinking desired for the particular application. Thus for example in the application as a support material for enzyme reactions in an agitator vessel or for diagnostic agents a relatively low degree of crosslinking is advantageous, requiring a low content of crosslinking monomer units. Crosslinker contents below 0.1% by weight lead in most cases to unusable products. The lower limit can therefore be given as generally about 1% by weight. Crosslinker contents above 60% by weight are possible in principle, but do not as a rule give any further advantages.

According to the application the amount of crosslinker units is preferably 1 to 50% by weight, and in particular 1 to 40% by weight, relative to the polymer.

In the use according to the invention as a support material for DAO, the lower limit is preferably 2.5% by weight, and particularly preferably 10% by weight. If only crosslinker units according to formula (II) are present, their lower limit is preferably 2.5% by weight.

It can be advantageous if the support polymer additionally contains monomer units of a monomer copolymerizable with vinyl acetate, where their amount generally does not exceed 10% by weight, relative to the total polymer, and is preferably between 0.1 and 5% by weight. Examples of such monomers, which may be used as a mixture, are: N-vinylpyrrolidone, vinylene carbonate, (meth)acrylic acid, (meth)acrylonitrile, (meth)acrylamide, alkyl (meth)acrylates each having 2 to 12 carbon atoms, preferably 2 to 4 carbon atoms, in the alkyl radical, hydroxyalkyl (meth)acrylates having 2 to 6 carbon atoms in the alkyl group, N-vinyl-N-alkylacetamide, styrene, α-methylstyrene and the like.

The crosslinked support polymer is preferably in the form of beads, of predominantly spherical shape, which have a mean particle size in the dry, unswollen state of 20 to 800 μm, preferably 50 to 300 μm, and which preferably have a narrow particle size distribution. The optimum particle size in each case depends principally on the specific application. For a column procedure not carried out under pressure, for example, the particle size selected within the limits mentioned previously will be correspondingly larger than that for a process carried out under pressure. The beads of the polymer used according to the invention are predominantly macroporous. The mean pore diameter is generally in the range from 2 to 10,000 nm, preferably 5 to 200 nm and in particular 20 to 200 nm.

The acylate groups of the vinyl acetate units in the polymer used according to the invention are present as such or all or some have preferably been hydrolyzed to OH groups. At least 10% by weight of the acyloxy groups are replaced by hydroxyl groups. However, the degree of hydrolysis is generally more than 50%, preferably more than 70% and in particular 90 to 100%. Crosslinked polymers obtained by hydrolysis (polyvinyl alcohol) preferably have at least some of the OH groups occupied by so-called spacer groups (with reference to spacers see below).

The copolymer in the form of a polyvinyl acetate gel is not hydrophilic; for use in water the ester group must be hydrolyzed. This can be achieved in known manner by alkali, by swelling the product in an alcohol, e.g. methanol, and adding aqueous alkali such as sodium hydroxide solution, or by transesterification of the alcohol-swollen product using catalytic amounts of acid or base and continuous removal, e.g. by distillation, of the ester formed (cf. German Patent 15 17 935). The hydrolysis can be terminated at any stage as required, so that the degree of hydrophilicity of the gel can be adjusted according to the application.

If the bead-shaped crosslinked polyvinyl alcohol gel is used as support for the DAO, which is to be attached to the support by a covalent bond, it is in many cases expedient previously to modify the gel with spacers. Spacers are taken to mean compounds that react with the support polymer and also with the biologically active substance, and to a certain extent form a bridge between the two. The reaction of the bead polymer with the spacer can be accomplished directly or preferably after previous hydrolysis of the acylate groups. The degree of conversion depends inter alia on the bulkiness of the spacer and the accessibility of the acylate group and/or of the resulting secondary hydroxyl groups. Spacers which can be used are, according to the invention, homo- and heterobifunctional compounds known for this purpose, whose second functional group is responsible for the coupling to the biologically active substance to be immobilized (cf. the German Patents 24 21 789 and 25 52 510, and also Ullmans Encyclopädie der technischen Chemie [Ullmann's Encyclopedia of Industrial Chemistry], 4th Edition, Vol. 10, page 540 and "Characterization of immobilized biocatalysts", Verlag Chemie, Weinheim, 1979, p.53).

The spacers used are for example compounds which introduce the following groups:

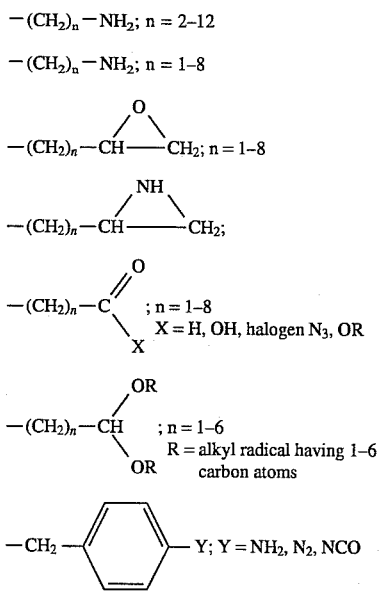

Preferred spacers are those that result in hydrolysis-resistant chemical compounds, such as epichlorohydrin or its homolog ($\alpha,\beta$-epoxy-$\omega$-haloalkanes). The reaction with polyvinyl alcohols (polyvinyl acylates) is carried out in the absence or presence of a solvent, preferably in the presence of a catalyst. The length of reaction is—depending on the temperature, which can be between room temperature and the reflux temperature of the epichlorohydrin (113°–115° C.)—generally between 30 minutes and 24 hours. The catalyst can be for example NaOH (in powder form) or aqueous alkalis, dimethylformamide, triethylamine and other acid acceptors.

The reaction between the DAO and the support material is carried out between 0° and +40° C., preferably at room temperature. The coupling reaction is preferably carried out at a fairly neutral pH, for example at a pH of from 5 to 9, preferably in the presence of phosphate buffers having an ionic strength of from 0.5 to 1.5 M.

D-amino acid oxidase can be isolated for example from hog kidneys, bacteria, yeasts or molds. Preference is given to the use of the DAO from the yeast *Trigonopsis variabilis* CBS 4095. Coupling to the enzyme support can be performed with purified, partially purified or crude DAO-containing cell extracts. The purification of DAO can be performed by conventional procedures, e.g. by ammonium sulfate precipitation, or ion exchange or gel permeation chromatography. Preference is given to the use of DAO-containing enzyme solutions obtained by ®DEAE-cellulose ion-exchange chromatography.

Furthermore, catalase can also be coupled to the enzyme support by means of the DAO. The catalase can be isolated for example from animals, bacteria, yeasts or molds. Preference is given to the use of the catalase from the yeast *Trigonopsis variabilis* CBS 4095. Coupling to the enzyme support can be performed with purified, partially purified or crude catalase-containing cell extracts. The catalase can be coupled to the enzyme support simultaneously with the DAO, or before or after the DAO. Enzyme supports coated only with DAO or only with catalase can also be mixed.

In the following, the invention is explained by using examples. Percentages given are by weight.

EXAMPLE 1

The cultures of *Trigonopsis variabilis* CBS 4095 were grown first in shaken flasks and subsequently in stirred fermenters containing the medium described by Sentheshanmuganathan and Nickerson (J. Gen. Microbiol. 27,465, 1962), and using either methionine or alanine as nitrogen source.

For DAO determination 0.4 g of cells is frozen, then thawed at acid pH, e.g. about pH 3–4; the freezing can be carried out at a temperature below –10° C., e.g. about –20° C. Freezing should be performed for a period sufficient to permeabilize the cells, e.g. at least 1 hour at –20° C.

The activity is determined photometrically using the following assay system:

| Solutions: | | |
|---|---|---|
| 1) buffer | | 100 mM PPB; pH 7.3; air-saturated |
| 2) o-phenylenediamine | | 0.02% in $H_2O$ |
| 3) peroxidase | | 1 mg/ml in buffer |
| 4) enzyme or permeabilized cells | | optimal: 0.5–1.0 units/ml |
| 5) substrate | | 150 mM Na—CPC (100%) in buffer |

Assay procedure:

$\lambda$ = 405 nm (maximum)
$\epsilon$ = 4020 l/mol*cm
$v$ = 30° C.

| Volume: | Final concentration: |
|---|---|
| 1) 2.00 ml | 83 mM |
| 2) 0.50 ml | 0.0034% |
| 3) 0.10 ml | 0.034 mg/ml |
| 4) 0.05 ml wait 2 min | |
| 5) 0.30 ml | 15.25 mM |
| 2.95 ml | |

Calculations:

$$\frac{\text{Units}}{\text{ml}} = \frac{\Delta E * \text{dilution} * \text{total volume}}{\text{min} * \xi * d * \text{sample volume}}$$

Under the conditions described above an enzyme activity in the fermenter of 200 U/l is achieved.

In the activity determinations using immobilized enzyme, samples are taken at intervals and the decrease in CPC concentration is determined by HPLC. The mobile phase comprises 40 mM potassium phosphate buffer (pH 4.3) and 20% of MeOH with 10 mg/l of tetrabutylammonium hydrogen sulfate. The stationary phase is ®Lichrospher 100 RP 18 (5 µm).

EXAMPLE 2

Synthesis of the supports a) Suspension polymerization

Under a nitrogen atmosphere in a 1.4 l glass flask having a stirrer, reflux condenser and thermometer an organic phase comprising a solution of 60.0 g of vinyl acetate, 40.0 g of N,N'-divinylethyleneurea, 80.0 g of 2-ethylhexanol, 20.0 g of Polyglykol B 11/50 (Hoechst AG) and 2.0 g of azoisobutyronitrile ®Porofor N (Bayer AG), was suspended with stirring in an aqueous phase comprising 3.2 g of $Na_2HPO_4$, 8.0 g of polyvinylpyrrolidone (molecular weight approximately 360,000) and 800 ml of water. The polymerization was started by heating to 75° C. in a heating bath. After two hours the temperature was increased to 85° C. and after a further two hours the polymerization was completed. The suspension obtained was cooled to 25° C., filtered off with suction and stirred for 30 minutes four times with 1 l of water each time, three times with 1 l of methanol each time and twice with 1 l of acetone each time, filtered off with suction and dried overnight at 50° C. and 200 mm Hg in a vacuum drying oven under nitrogen. The yield was 75 g. Cloudy beads with a glossy surface were obtained. The bulk density was 300 g/l. This gives a bulk volume of 3.3 ml/g.

b) Partial hydrolysis 50 g of dry product and 150 ml of methanol and a solution of 17.5 g of NaOH in 150 ml of water were stirred for 3 hours at 30° C., filtered off with suction, neutralized in 500 ml of methanol with acetic acid, stirred once with 500 ml of methanol and twice each with 500 ml of acetone, filtered off with suction, sieved and dried. The yield was 34.4 g (=68.8% by weight) based on the polymer. The beads were cloudy and had a glossy surface. The bulk density was 353 g/l (calculated bulk volume 2.8 ml/g). Sieving distribution: >300 µm 19.0 g (55.2% by weight), 200–300 µm 8.9 g (25.9% by weight), 100–200 µm 6.1 g (17.9% by weight) and 50–100 µm 0.4 g (1.2% by weight). Degree of hydrolysis (IR, molar basis): 73%.

c) Attachment of the spacer 10.0 g of the dry 50–200 µm sieve fraction were swollen for 4 hours in 100 ml of epichlorohydrin at 25° C., then heated for 4 hours with gentle stirring to 115° C., and, after cooling to 25° C., filtered off with suction. Then the mixture was stirred twice with 200 ml of acetone each time for 30 minutes, filtered off with suction and kept overnight in a drying oven under reduced pressure at 50° C. under nitrogen.

9.8 g of dry product was obtained having a bulk density of 315 g/l and an epoxide equivalent of 350 µmol/g.

EXAMPLE 3

To 10 g of wet cells produced as in Example 1 having an activity of 30 U/g are added the same weight of 20 mM potassium phosphate buffer, pH 8.0, giving a suspension. The mixture is ground in a cooled Dyno mill at a residence time of 3×5 min. The yield of activity in the supernatant after centrifugation at 13,000 g is 60 to 80%; on average that is 210 U. The slightly cloudy crude extract is dialyzed against a 20 mM potassium phosphate buffer, pH 8.0. Sufficient DEAE-cellulose from Whatman is then added to bind the DAO completely. The bound enzyme is subsequently poured into a column and the DAO is eluted with increasing ionic strength (0–0.5 M NaCl). The active fractions are combined, concentrated by ultrafiltration and rebuffered with 1M potassium phosphate buffer (pH=8.0). On average, the DAO solution purified in this manner contains 25 U/ml.

EXAMPLE 4

5 ml of a solution obtained according to Example 3 are added to 1 g of VA-EpoxyBiosynth® from Riedel de Haen and allowed to stand in a sealed container for 3 days at room temperature. During this time the enzyme binds covalently to the oxirane group-containing support. The immobilized enzyme is then washed with 1M NaCl solution. The mean binding efficiency is 0.83. Small amounts are in the washing water. The immobilized enzyme contains approximately 32 U/g (wet weight, wwt). It is stored in a 20 mM potassium phosphate buffer, containing 0.02% of sodium azide, at 4 degrees Celsius.

EXAMPLE 5

As Example 2, but the support used is Eupergit® from R öhm, Darmstadt. Result in Table 1.

EXAMPLE 6

2 ml of DAO solution are dialyzed against a 50 mM potassium phosphate buffer (pH=8.6). The buffered solution having a total of 60 U is incubated at room temperature (RT) for 18 h with 2 ml of vinyl-Sepharose suspension (60%) to effect immobilization. 1.2 ml of Sepharose containing 22 U/ml are obtained (see Table 1), corresponding to an immobilization yield of 43%. 10 U are present in the washing water, so that a value η of 0.51 is calculated.

EXAMPLE 7

1 ml of DAO solution containing 3.2 U, which had been dialyzed against 0.5 M potassium phosphate buffer, pH 8.7, are added to 0.2 g of CNBr-activated Sepharose (Pharmacia) at RT. After 90 min the coupling is completed, and the support is washed in accordance with the manufacturer's instructions. Excess binding groups are inactivated with glycine. Result see Table 1.

EXAMPLE 8

The enzyme immobilized as in Example 4 is stored under the conditions given in Example 4 and its activity was measured each month. In 6 months the activity does not decrease by more than 5%.

EXAMPLE 9

Sodium cephalosporin C (40 mM) is dissolved at pH 7.3 in 20 mM potassium phosphate buffer, and the solution is thermostated to 30° C. with stirring and treated with oxygen. 2% (w/w) of immobilized DAO are added to this and the mixture is maintained at the initial pH by means of an autotitrator. After completion of the reaction, the solution is drained off and the reactor is refilled. The enzyme remains in the vessel. The number of reactions is 120. The reaction time is selected so that complete conversion is possible. This is 1 hour up to about 40 reactions, then 1.5 up to 90, and finally 2 h.

TABLE 1

Comparison of enzyme supports

| | Binding efficiency [η] | U/g (wwt) | $t_d$ at 30°, pH = 7.3 |
|---|---|---|---|
| Eupergit (Röhm) | 0.71 | 29 | ≈20 |
| Va-Epoxy (Riedel de Haen) | 0.83 | 32 | >40 |
| Vinyl-Sepharose (Kem-en-tec) | 0.51 | 22 | ≈15 |
| BrCN-activated Sepharose (Pharmacia) | 0.7 | 6 | ≈6 |

I claim:

1. An enzyme-coated support material comprising D-amino acid oxidase purified by ion exchange chromatography from *Trigonopsis variabilis* and a porous bead-shaped support material, wherein the support material is a crosslinked copolymer consisting essentially of vinyl acetate units and units of a crosslinking agent, having the formula:

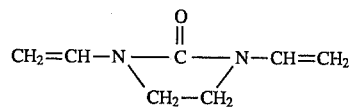

the amount of crosslinking agent is 1% to 60% by weight, relative to the copolymer, the acyloxy groups of the vinyl acetate units are present as such, or some or all have been hydrolyzed to hydroxyl groups, the bead-shaped support material has a mean particle size of 20 to 800 μm and a mean pore diameter of 20 to 10,000 nm, and the bead-shaped support material is modified with a spacer group of the formula:

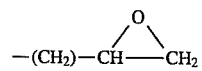

to which the D-amino acid oxidase is covalently bound.

* * * * *